(12) United States Patent
Sgroi, Jr. et al.

(10) Patent No.: US 11,529,144 B2
(45) Date of Patent: Dec. 20, 2022

(54) ENCAPSULATED PLUG ASSEMBLY FOR ELECTROMECHANICAL SURGICAL DEVICES

(71) Applicant: Covidien LP, Mansfield, MA (US)

(72) Inventors: Anthony Sgroi, Jr., Wallingford, CT (US); David Valentine, Jr., Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 317 days.

(21) Appl. No.: 16/773,424

(22) Filed: Jan. 27, 2020

(65) Prior Publication Data
US 2020/0268390 A1      Aug. 27, 2020

Related U.S. Application Data

(60) Provisional application No. 62/808,925, filed on Feb. 22, 2019.

(51) Int. Cl.
*A61B 17/115*     (2006.01)
*A61B 17/00*      (2006.01)

(52) U.S. Cl.
CPC . *A61B 17/1155* (2013.01); *A61B 2017/00398* (2013.01); *A61B 2017/00907* (2013.01); *A61B 2560/02* (2013.01); *A61B 2562/222* (2013.01)

(58) Field of Classification Search
CPC .. H01R 43/24; H01R 13/5205; H01R 12/772; A61B 17/1155; A61B 17/07207; A61B 17/105; A61B 17/068
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report dated Jul. 22, 2020 corresponding to counterpart Patent Application EP 20158699.7.

(Continued)

*Primary Examiner* — Nathaniel C Chukwurah

(57) ABSTRACT

A plug assembly for an electromechanical surgical system includes: a housing defining a proximal facing bore; a pair of electrical contacts disposed within the housing, each electrical contact including a distal end portion projecting distally from a distal end of the housing; and a proximal end portion disposed within the proximal facing bore of the housing; a ribbon cable having a distal end portion electrically connected to the proximal end portion of each of the pair of electrical contacts, and being disposed with the proximal facing bore of the housing; and an encapsulating material filling the proximal facing bore of the housing.

17 Claims, 14 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |

(56) References Cited

U.S. PATENT DOCUMENTS

| | | | |
|---|---|---|---|
| 7,942,302 B2 | 5/2011 | Roby et al. | |
| 7,951,166 B2 | 5/2011 | Orban, III et al. | |
| 7,959,050 B2 | 6/2011 | Smith et al. | |
| 7,967,181 B2 | 6/2011 | Viola et al. | |
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,007,302 B2 * | 8/2011 | Kleinke | H01R 9/03 439/589 |
| 8,011,551 B2 | 9/2011 | Marczyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,109,426 B2 | 2/2012 | Milliman et al. | |
| 8,109,427 B2 | 2/2012 | Orban, III | |
| 8,113,405 B2 | 2/2012 | Milliman | |
| 8,113,406 B2 | 2/2012 | Holsten et al. | |
| 8,113,407 B2 | 2/2012 | Holsten et al. | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter, III et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,453,910 B2 | 6/2013 | Bettuchi et al. | |
| 8,453,911 B2 | 6/2013 | Milliman et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,551,138 B2 | 10/2013 | Orban, III et al. | |
| 8,567,655 B2 | 10/2013 | Nalagatla et al. | |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,662,370 B2 | 3/2014 | Takei | |
| 8,663,258 B2 | 3/2014 | Bettuchi et al. | |
| 8,672,931 B2 | 3/2014 | Goldboss et al. | |
| 8,678,264 B2 | 3/2014 | Racenet et al. | |
| 8,684,248 B2 | 4/2014 | Milliman | |
| 8,684,250 B2 | 4/2014 | Bettuchi et al. | |
| 8,684,251 B2 | 4/2014 | Rebuffat et al. | |
| 8,684,252 B2 | 4/2014 | Patel et al. | |
| 8,733,611 B2 | 5/2014 | Milliman | |
| 2003/0054693 A1 | 3/2003 | Fuchs et al. | |
| 2003/0111507 A1 | 6/2003 | Nunez | |
| 2004/0073090 A1 | 4/2004 | Butler et al. | |
| 2005/0051597 A1 | 3/2005 | Toledano | |
| 2005/0107813 A1 | 5/2005 | Gilete Garcia | |
| 2006/0000869 A1 | 1/2006 | Fontayne | |
| 2006/0011698 A1 | 1/2006 | Okada et al. | |
| 2006/0032653 A1 | 2/2006 | Minoshima et al. | |
| 2006/0201989 A1 | 9/2006 | Ojeda | |
| 2006/0207092 A1 * | 9/2006 | Perle | H01R 13/405 29/877 |
| 2006/0246779 A1 * | 11/2006 | Helbok | H01R 43/24 439/606 |
| 2007/0027473 A1 | 2/2007 | Vresh et al. | |
| 2007/0029363 A1 | 2/2007 | Popov | |
| 2007/0049084 A1 | 3/2007 | Geismayr et al. | |
| 2007/0060952 A1 | 3/2007 | Roby et al. | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0147432 A1 | 6/2011 | Heinrich et al. | |
| 2011/0192882 A1 | 8/2011 | Hess et al. | |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0029541 A1 | 1/2013 | Chiarelli et al. | |
| 2013/0032628 A1 | 2/2013 | Li et al. | |
| 2013/0056516 A1 | 3/2013 | Viola | |
| 2013/0060258 A1 | 3/2013 | Giacomantonio | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0126580 A1 | 5/2013 | Smith et al. | |

(56) References Cited

U.S. PATENT DOCUMENTS

| | | |
|---|---|---|
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2018/0233850 A1 | 8/2018 | Penna et al. |
| 2019/0321033 A1 | 10/2019 | Sgroi, Jr. |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3011915 A2 | 4/2016 |
| EP | 3078335 A1 | 10/2016 |
| EP | 3165180 A2 | 5/2017 |
| EP | 3175800 A1 | 6/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

OTHER PUBLICATIONS

Clipsal Electrical Accessories: "Plugs, Sockets and Adaptors", May 2, 2005 (May 2, 2005), XP055714028, Retrieved from the Internet: URL:http://updates.clipsal.com/clipsalonline/files/brochures/a0000123.pdf [retrieved on Jul. 13, 2020]; 52 pages.

Christian Maletzko et al: "Polyarylsulfones (PSU, PESU, PPSU)", Kunststoffe International, Oct. 31, 2011 (Oct. 31, 2011), XP055714146, Retrieved from the Internet: URL:https://www.kunststoffe.de/en/storage/asset/625723/storage/master/file/6242354/download/Polyarylsulfones%20(PSU,%20PESU,%20PPSU).pdf [retrieved on Jul. 13, 2020]; 5 pages.

Extended European Search Report from Appl. No. 14181908.6 dated May 26, 2015.

European Examination Report from Appl. No. 14181908.6 dated May 3, 2016.

Extended European Search Report dated Oct. 31, 2018 issued in corresponding EP Appln. No 18176776.5.

European Examination Report dated Oct. 23, 2019 issued as EP Application No. 18176776.5.

* cited by examiner

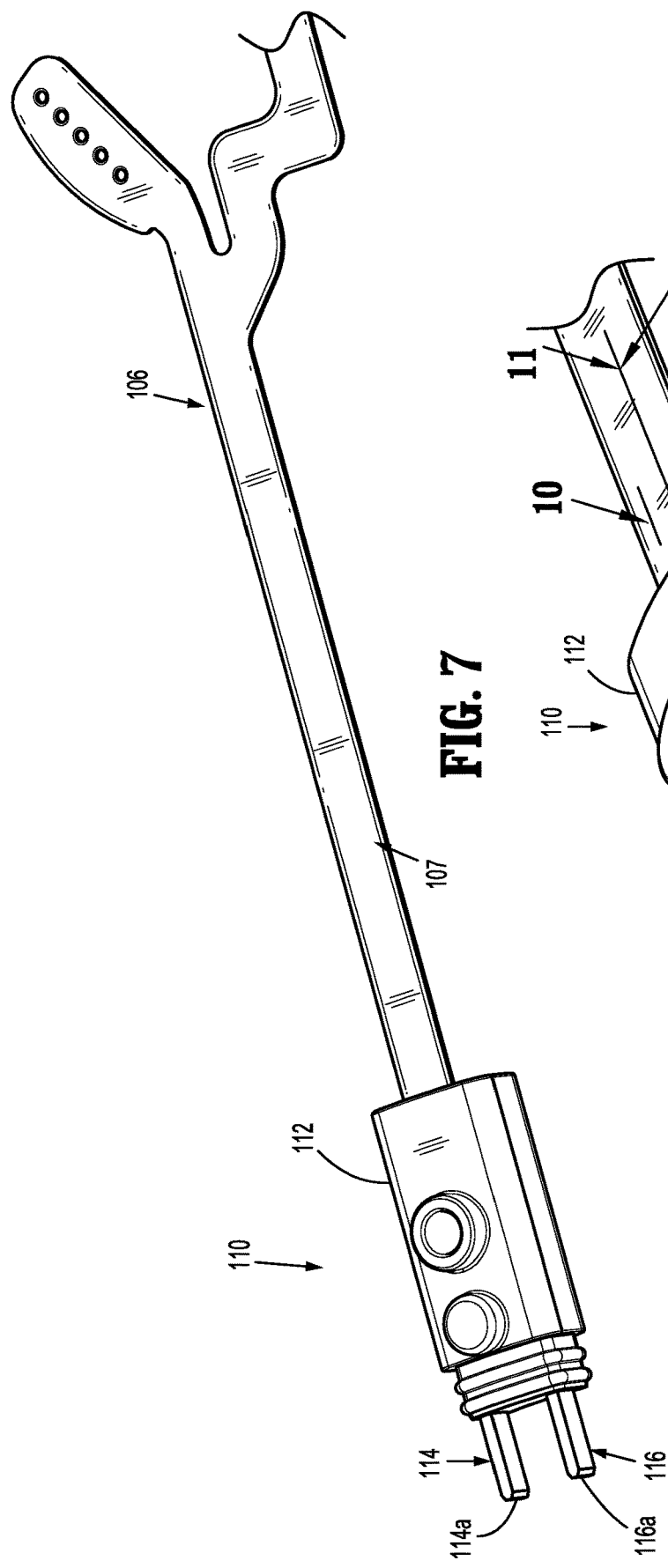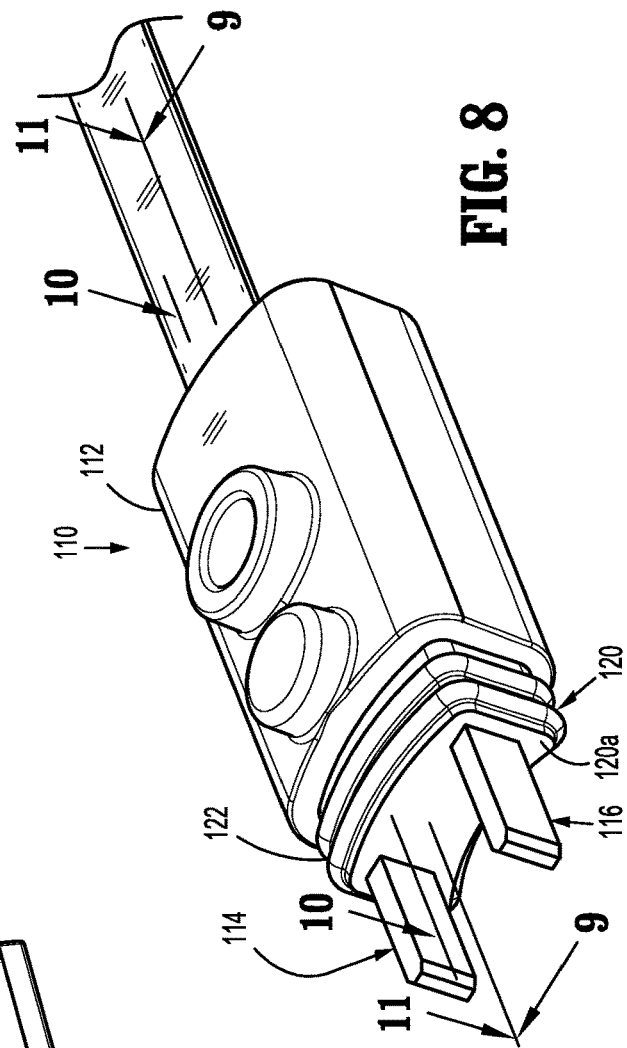

ENCAPSULATED PLUG ASSEMBLY FOR ELECTROMECHANICAL SURGICAL DEVICES

CROSS-REFERENCE TO RELATED APPLICATIONS

This application claims the benefit of and priority to U.S. Provisional Patent Application Ser. No. 62/808,925 filed Feb. 22, 2019, the entire disclosure of which is incorporated by reference herein.

BACKGROUND

1. Technical Field

The present disclosure relates to surgical devices. More specifically, the present disclosure relates to handheld electromechanical surgical systems for performing surgical procedures having an encapsulated plug assembly therein.

2. Background of Related Art

One type of surgical device is a circular clamping, cutting and stapling device. Such a device may be employed in a surgical procedure to reattach rectum portions that were previously transected, or similar procedures. Conventional circular clamping, cutting, and stapling devices include a pistol or linear grip-styled structure having an elongated shaft extending therefrom and a staple cartridge supported on the distal end of the elongated shaft. In this instance, a physician may insert the loading unit portion of the circular stapling device into a rectum of a patient and maneuver the device up the colonic tract of the patient toward the transected rectum portions. The loading unit includes a cartridge assembly having a plurality of staples. Along the proximal portion of the transected colon, an anvil assembly can be purse stringed therein. Alternatively, if desired, the anvil portion can be inserted into the colon through an incision proximal to the transected colon. The anvil and cartridge assemblies are approximated toward one another and staples are ejected from the cartridge assembly toward the anvil assembly thereby forming the staples in tissue to affect an end-to-end anastomosis, and an annular knife is fired to core a portion of the clamped tissue portions. After the end-to-end anastomosis has been effected, the circular stapling device is removed from the surgical site.

A number of surgical device manufacturers have also developed proprietary powered drive systems for operating and/or manipulating the end effectors. The powered drive systems may include a powered handle assembly, which may be reusable, and a disposable end effector that is removably connected to the powered handle assembly.

Many of the existing end effectors for use with existing powered surgical devices and/or handle assemblies are driven by a linear driving force. For example, end effectors for performing endo-gastrointestinal anastomosis procedures, end-to-end anastomosis procedures and transverse anastomosis procedures, are actuated by a linear driving force. As such, these end effectors are not compatible with surgical devices and/or handle assemblies that use rotary motion.

In order to make the linear driven end effectors compatible with powered surgical devices that use a rotary motion to deliver power, a need exists for adapters to interconnect the linear driven end effectors with the powered rotary driven surgical devices. These adapters may also be reusable, and as such, need to able to withstand multiple sterilization cycles.

As these adapters are becoming more sophisticated and include various electronic components, there is a need for electronic components disposed within the adapters that can withstand multiple autoclave cycles. For example, the electronic components may include flex or ribbon cables fabricated out of a material that is highly resistant to the high pH environments of disinfecting chemicals, such as, potassium hydroxide (KOH), and can also resist high temperature autoclave steam and the associated pressures of the autoclave (+atm/−atm). It is also desired that the housing of these electronic components also be fabricated out of a material that is highly resistant to the high PH environments of disinfecting chemicals (KOH) and that can also resist high temperature autoclave steam and the associated pressures of autoclave (+atm/−atm).

SUMMARY

According to one embodiment of the present disclosure, a plug assembly for an electromechanical surgical system is disclosed. The plug assembly includes: a housing defining a proximal facing bore; a pair of electrical contacts disposed within the housing, each electrical contact including a distal end portion projecting distally from a distal end of the housing; and a proximal end portion disposed within the proximal facing bore of the housing; a ribbon cable having a distal end portion electrically connected to the proximal end portion of each of the pair of electrical contacts, and being disposed with the proximal facing bore of the housing; and an encapsulating material filling the proximal facing bore of the housing.

According to another embodiment of the present disclosure, the plug assembly includes: a housing defining a proximal facing bore, the housing including a proximally extending central rib located within the proximal facing bore; a pair of electrical contacts disposed within the housing, wherein the pair of electrical contacts are spaced apart from one another, each electrical contact including a distal end portion projecting distally from a distal end of the housing; and a proximal end portion disposed within the proximal facing bore of the housing; a ribbon cable having an axially split distal end portion defining a pair of fingers spaced apart from one another by a gap, each finger being electrically connected to the proximal end portion of a respective one of the pair of electrical contacts, and being disposed with the proximal facing bore of the housing, wherein the rib of the housing is disposed within the gap of the ribbon cable; and an encapsulating material filling the proximal facing bore of the housing.

The housing may be at least partially transparent. The housing may be transparent for light or UV curing. The housing may be fabricated from polyphenylsulfone (PPSU) or polysulfone (PSU).

The encapsulating material may be a light or UV curable material. The encapsulating material may be resin or acrylic resin.

The housing may define a distal facing bore therein. The plug assembly may further include a seal member disposed within the distal facing bore of the housing.

The housing and the seal member may form a fluid-tight seal therebetween. The seal member may be fabricated from silicone, rubber, plastic or polymer.

The seal member may include a distal portion projecting distally from the housing, and a proximal portion extending from a side surface of the housing.

The distal end portion of each of the pair of electrical contacts may extend distally beyond the seal member.

The seal member may include at least one circumferential ridge extending therearound.

Each electrical contact may include a nub projecting from the proximal end portion thereof. The distal end portion of the ribbon cable may define a respective solder recess formed therein for receipt of a respective nub.

Each electrical contact may include a pair of nubs projecting from the proximal end portion thereof. The distal end portion of the ribbon cable may define a respective pair of solder recesses formed therein for receipt of a respective pair of nubs.

Each electrical contact may include a nub projecting from the proximal end portion thereof. Each finger of the distal end portion of the ribbon cable may define a respective solder recess formed therein for receipt of a respective nub.

Each electrical contact may include a pair of nubs projecting from the proximal end portion thereof. Each finger of the distal end portion of the ribbon cable may define a respective pair of solder recess formed therein for receipt of a respective pair of nubs.

BRIEF DESCRIPTION OF THE DRAWINGS

Embodiments of the present disclosure are described herein with reference to the accompanying drawings, wherein:

FIG. 7 is an enlarged view of a distal portion of the electrical assembly of FIGS. 5 and 6;

FIG. 8 is a distal, perspective view of a plug assembly of the electrical assembly of FIGS. 1-7, configured for connection to the reload of the handheld surgical device;

DETAILED DESCRIPTION OF EMBODIMENTS

Figure 1:
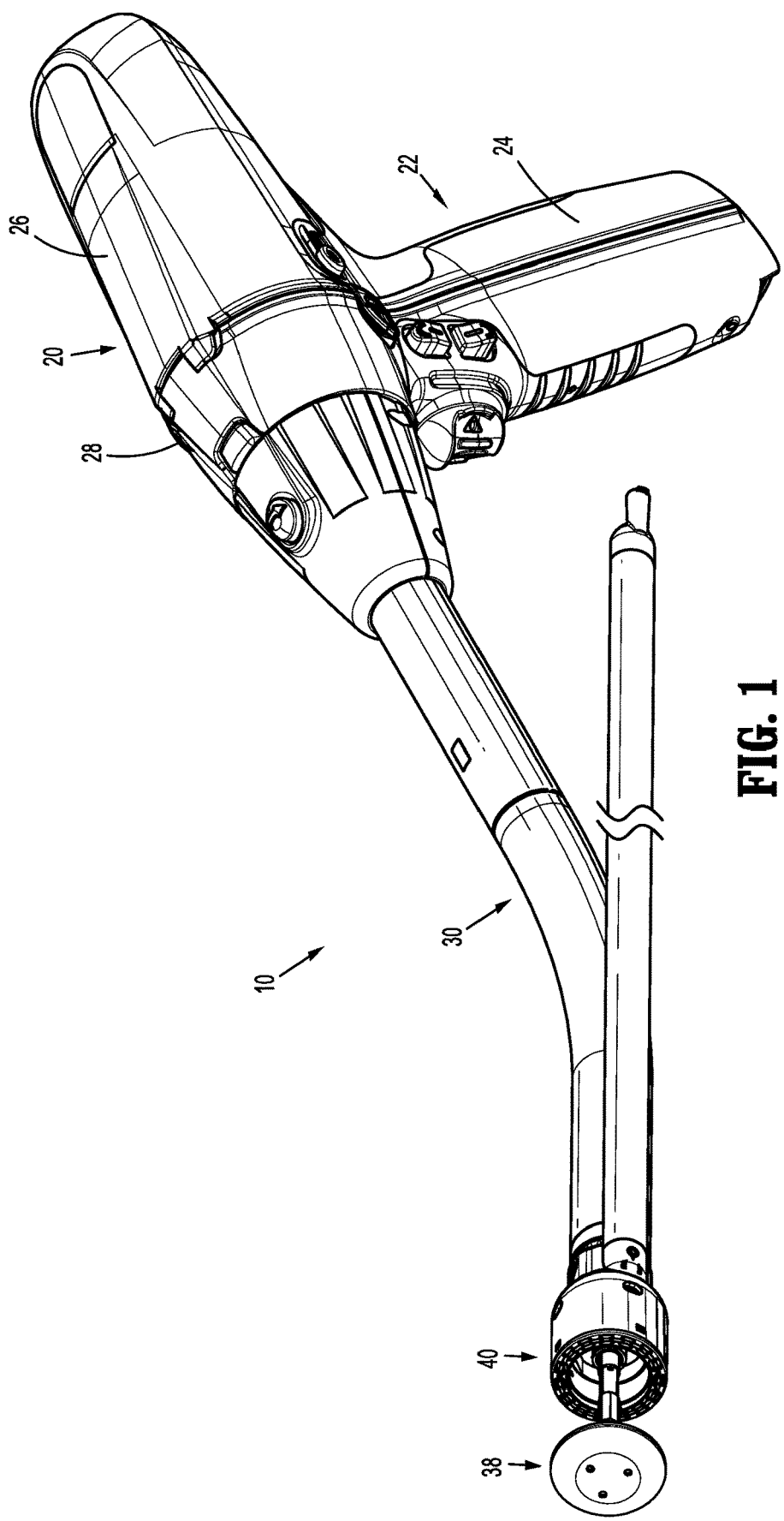
FIG. 1 is a perspective view of a handheld surgical device, an adapter assembly, an end effector having a reload and an anvil assembly according to an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure relates to powered surgical devices having electronic sensors for monitoring mechanical strain and forces imparted on components of the powered surgical devices. More particularly, this disclosure relates to load measuring sensors including load sensing devices as well as analog and digital circuitry that are hermetically sealed such that the load sensors are configured to resist harsh environments. In the event that electrical connections of the powered surgical devices are compromised during use, measurement signals output by the sensors of the present disclosure remain unaltered. In addition, the sensors are programmable allowing for adjustments to gain and offset values in order to optimize the measurement signals.

With reference to FIG. 1, a powered surgical device 10 includes a handle assembly 20, which is configured for selective connection with an adapter assembly 30, which in turn, is configured for selective connection with an end effector, such as an annular reload 40. Although generally referred to as being a powered surgical device, it is contemplated that the surgical device 10 may be a manually actuated and may include various configurations.

Figure 2:
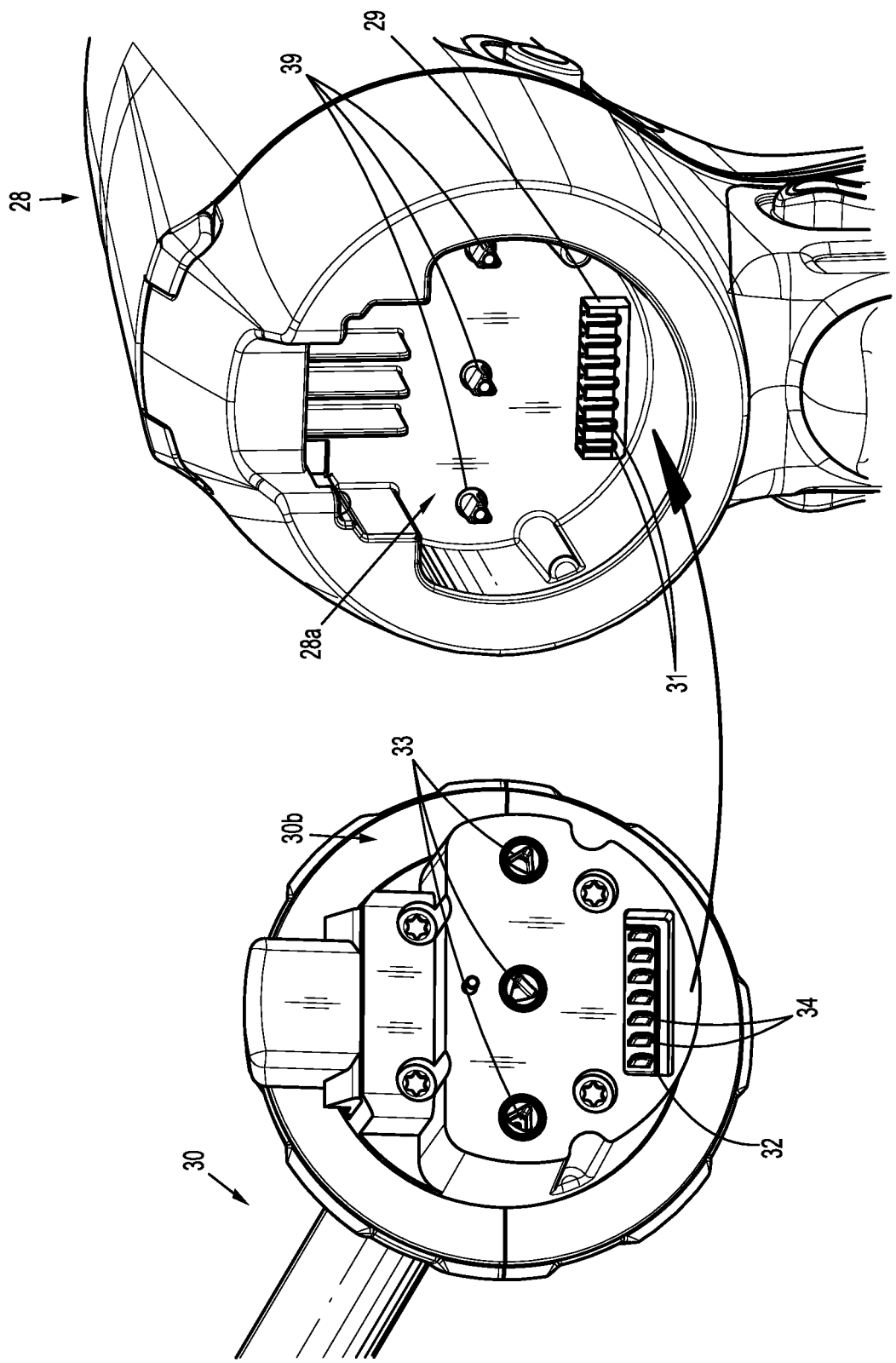
FIG. 2 is a perspective view illustrating a connection of the adapter assembly and the handle assembly of FIG. 1 according to an embodiment of the present disclosure.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. As shown in FIG. 2, a distal portion of the upper housing portion 28 defines a nose or connecting portion 28a that is configured to accept a proximal end portion 30b of the adapter assembly 30.

Figure 3:
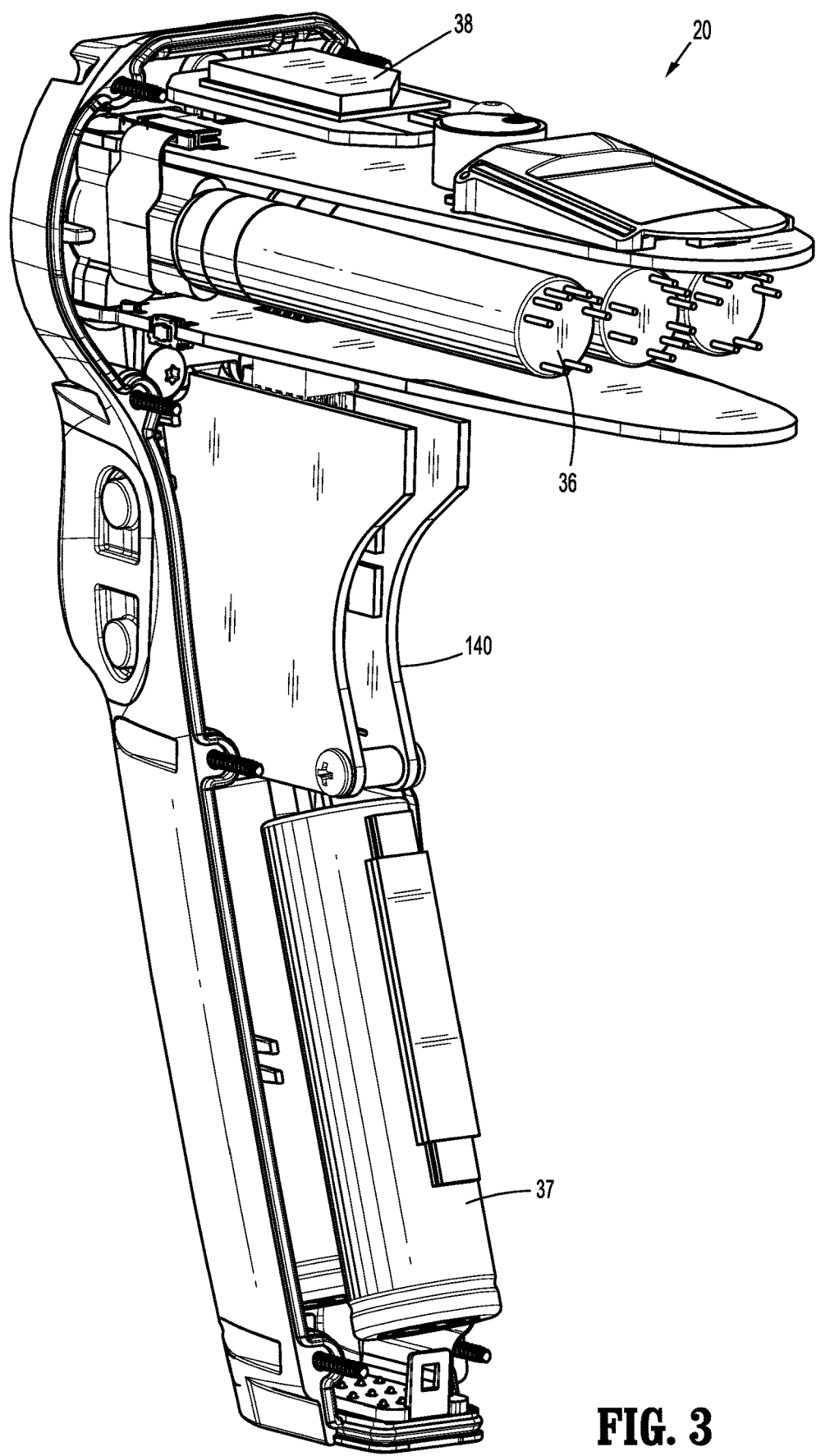
FIG. 3 is perspective view of internal components of the handle assembly according to an embodiment of the present disclosure.

With reference to FIG. 3, the handle assembly 20 includes one or more motors 36 which are coupled to a battery 37. The handle assembly 20 also includes a main controller 38 for operating the motors 36 and other electronic components of the handle assembly 20, the adapter assembly 30, and the reload 40. The motors 36 are coupled to corresponding drive shafts 39 (FIG. 2), which are configured to engage sockets 33 on the proximal end portion 30b, such that rotation of the drive shafts 39 is imparted on the sockets 33.

Figure 4:
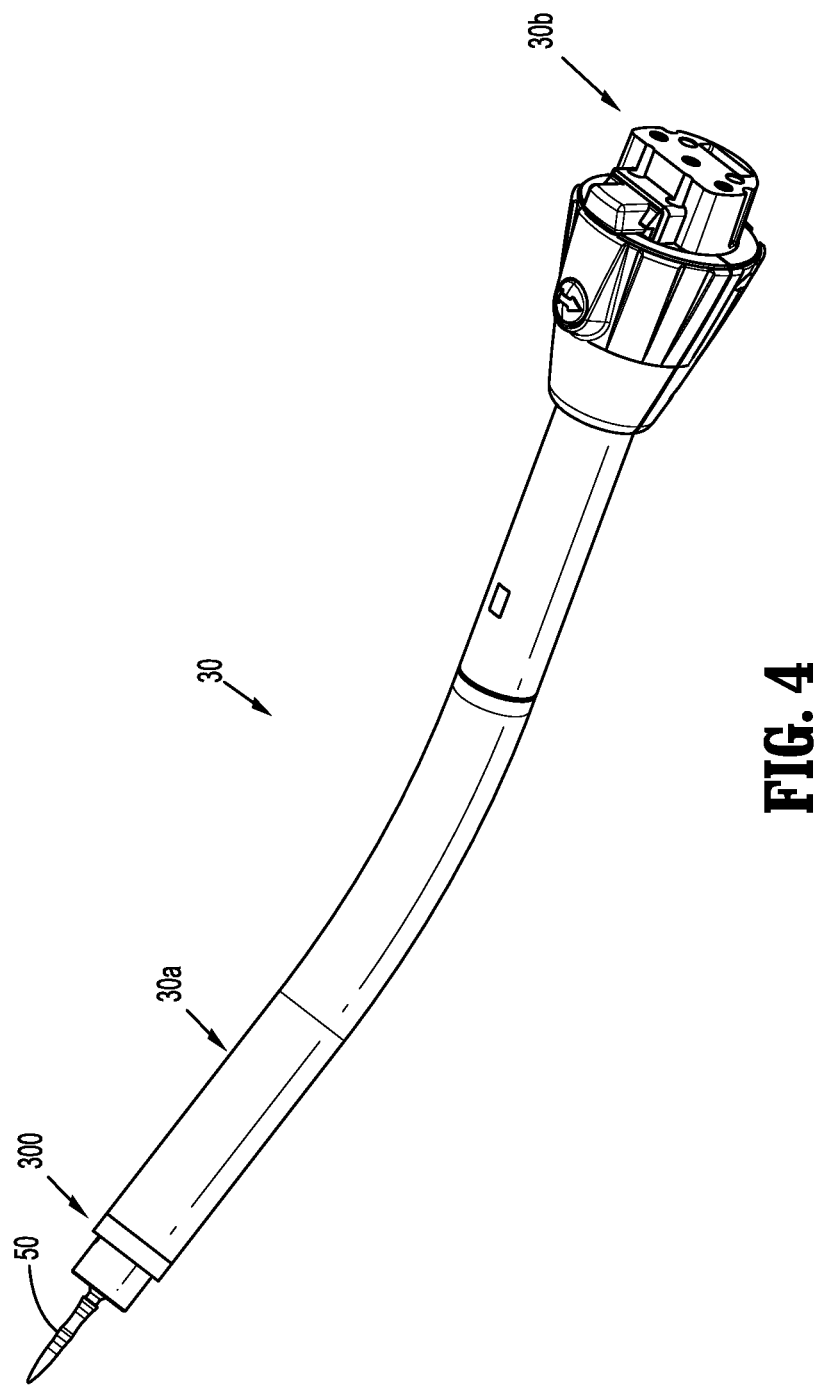
FIG. 4 is a perspective view of the adapter assembly of FIG. 1 without the reload according to an embodiment of the present disclosure.
Figure 5:
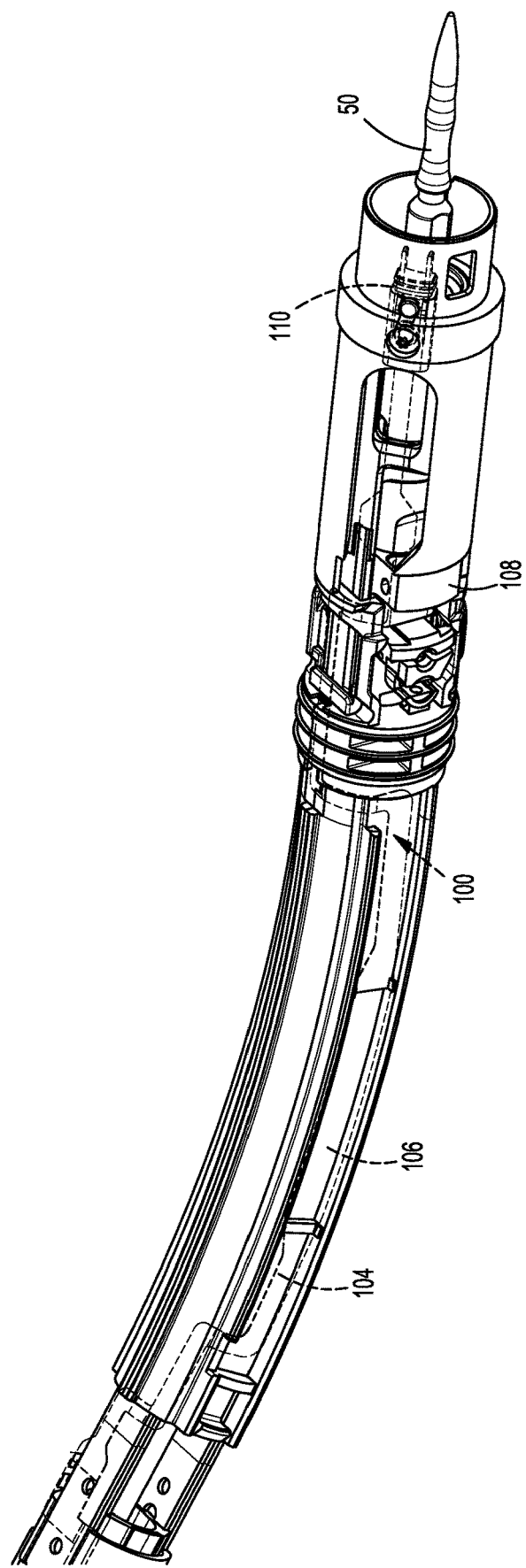
FIG. 5 is a perspective view of a distal end portion of the adapter assembly of FIGS. 1-4, illustrating an electrical assembly thereof, in accordance with an embodiment of the present disclosure.
Figure 6:
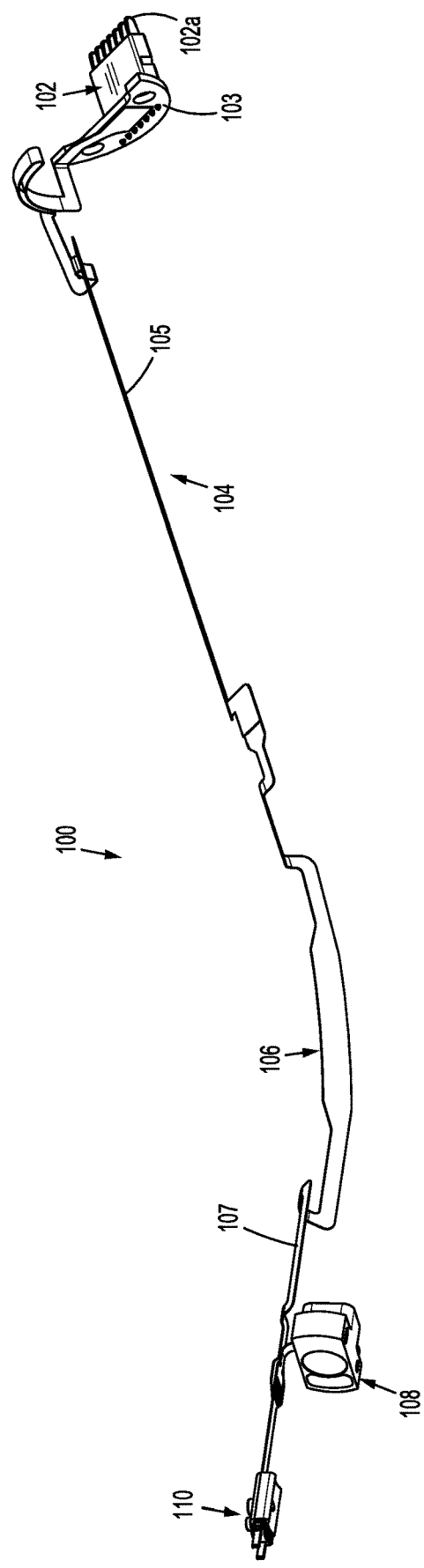
FIG. 6 is a perspective view of the electrical assembly of the adapter assembly of the present disclosure.
Figure 9:
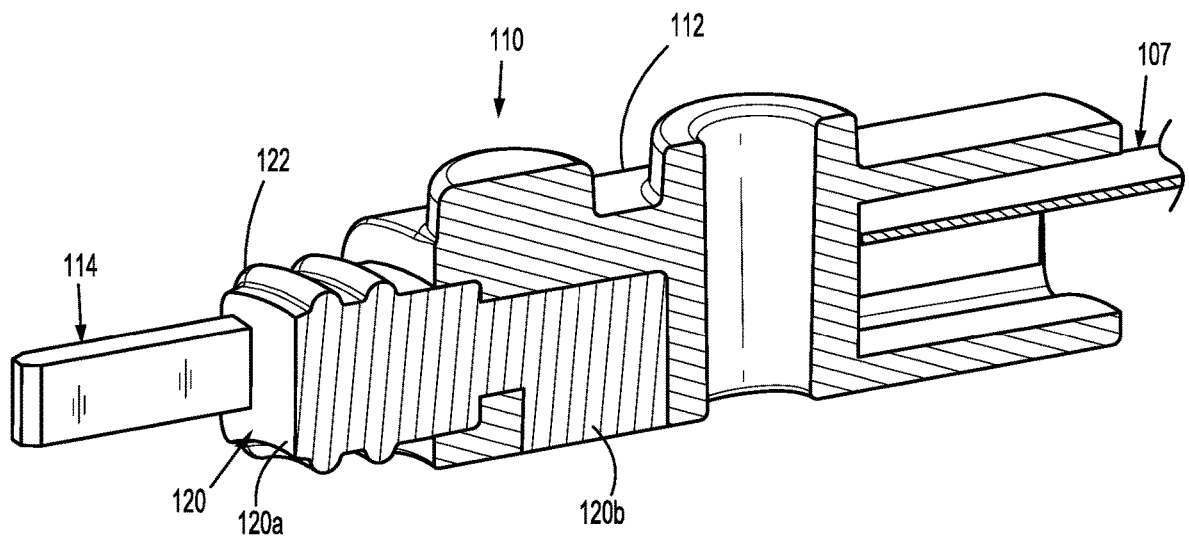
FIG. 9 is a cross-section view of the plug assembly of FIG. 8, as taken through 9-9 of FIG. 8.
Figure 10:
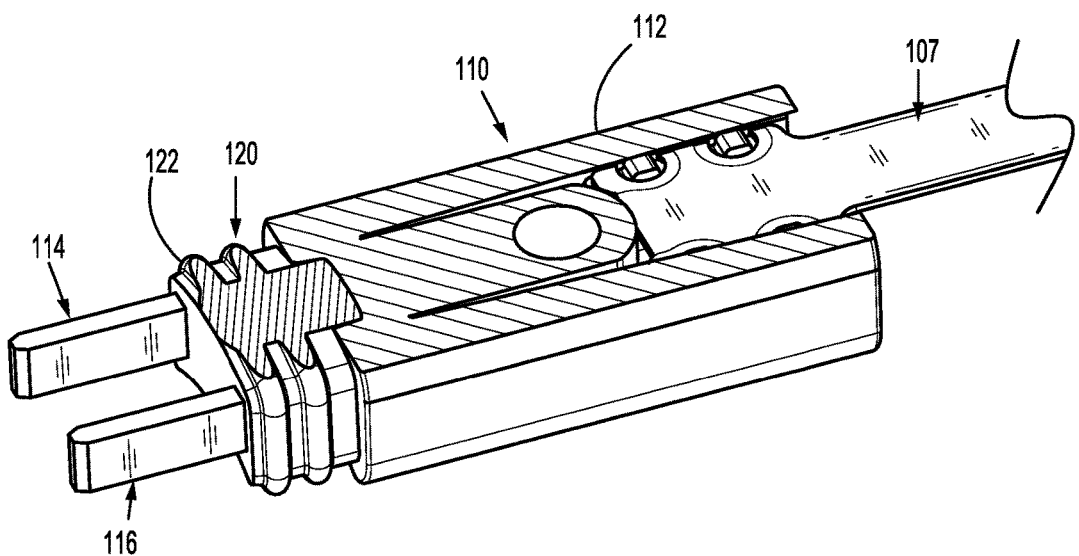
FIG. 10 is a cross-section view of the plug assembly of FIG. 8, as taken through 10-10 of FIG. 8.
Figure 11:
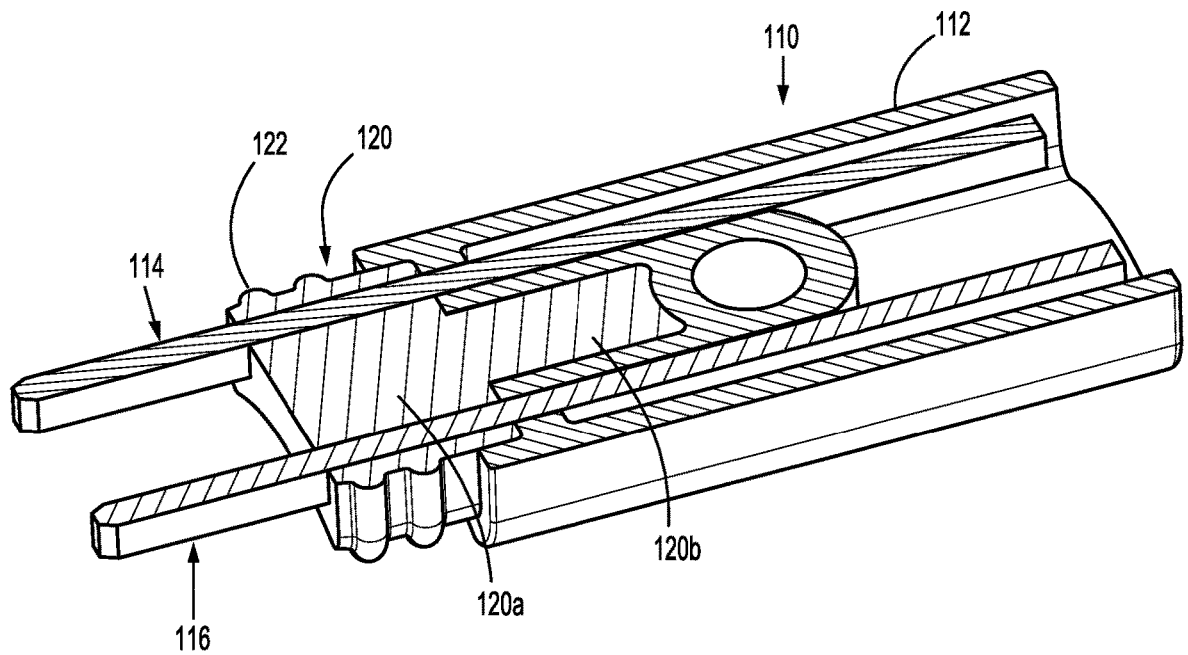
FIG. 11 is a cross-section view of the plug assembly of FIG. 8, as taken through 11-11 of FIG. 8.
Figure 12A:
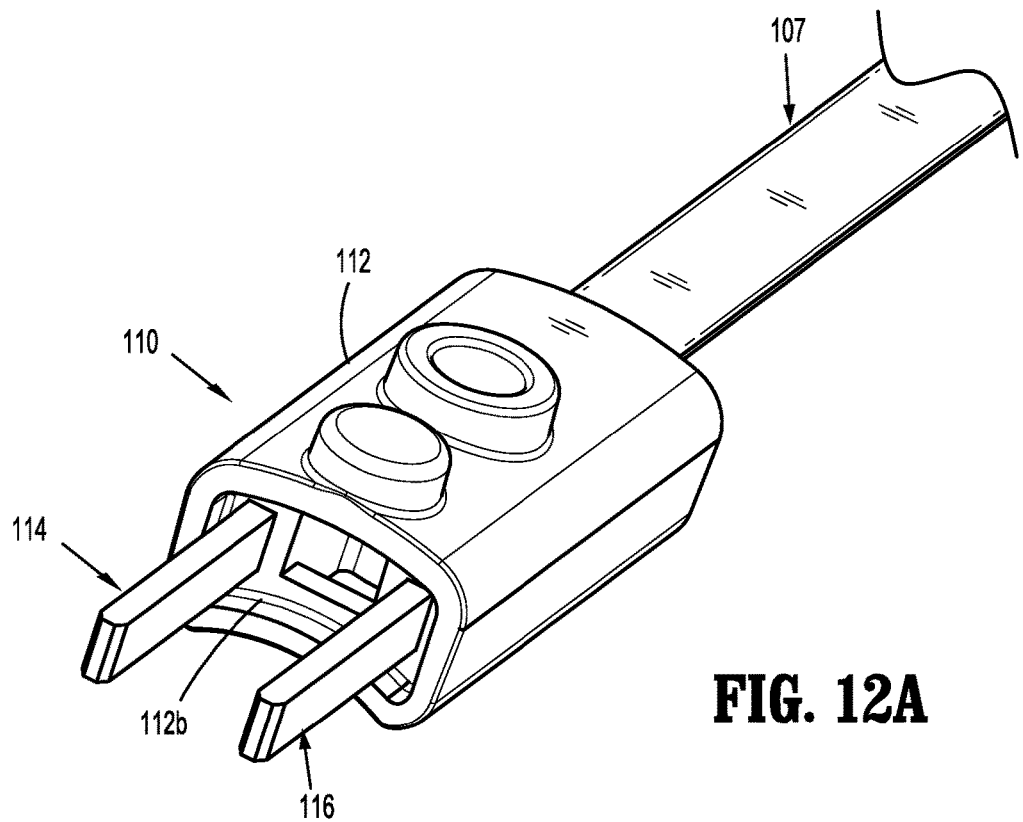
FIGS. 12A and 12B are rear and front perspective views, respectively, of the plug assembly of FIG. 8, with a seal removed therefrom.
Figure 12B:
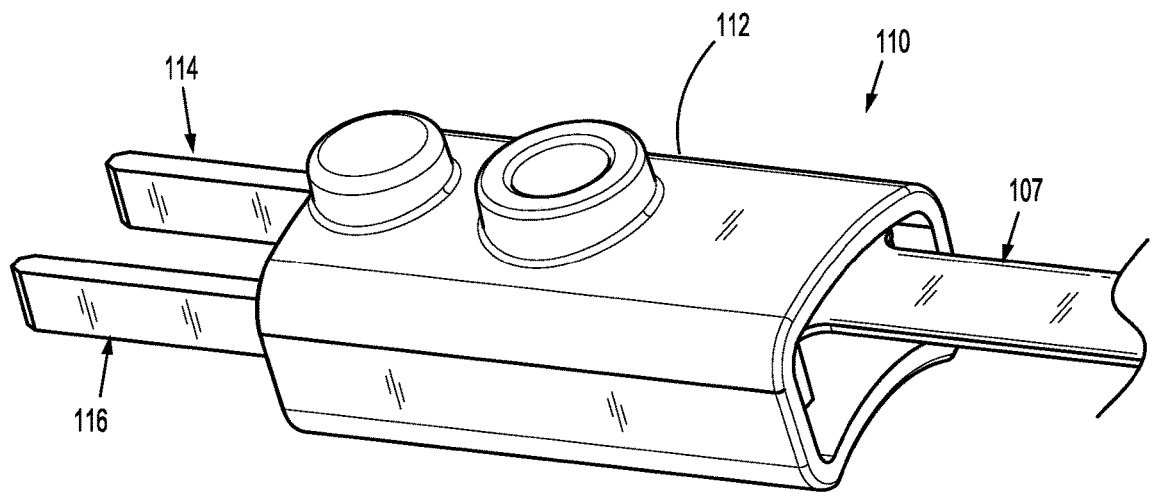
Figure 13:
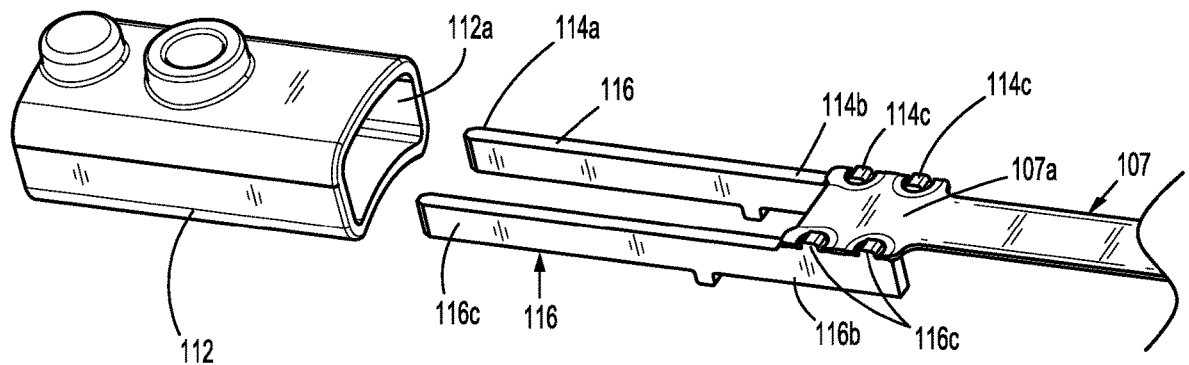
FIG. 13 is a perspective view of the plug assembly of FIG. 8, illustrating an insertion of a ribbon cable and contacts into a housing, of the plug assembly.
Figure 14:
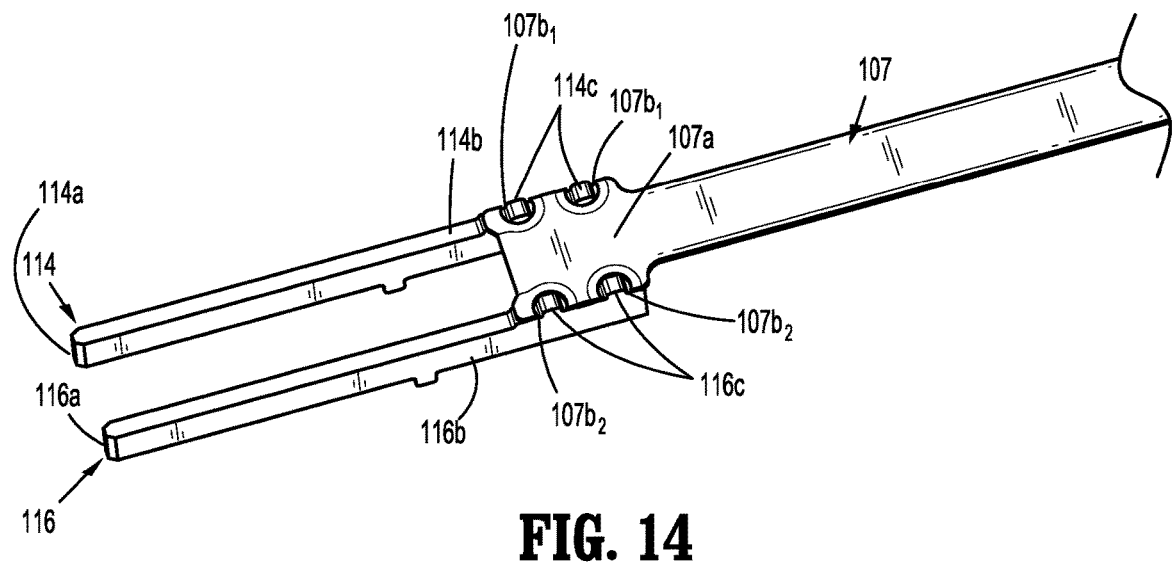
FIG. 14 is a perspective view of the ribbon cable and contacts of the plug assembly of FIG. 8.

With reference to FIG. 4, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the reload 40. In this manner, the adapter assembly 30 is configured to convert a rotational motion provided by the handle assembly 20 into axial translation useful for advancing/retracting a trocar member 50 slidably disposed within the distal end portion 30c of the adapter assembly 30 for actuating functions of the reload 40, e.g., such as, for firing staples of the reload 40.

With reference to FIG. 2, the connecting portion 28a includes an electrical receptacle 29 having a plurality of electrical contacts 31, which are in electrical communication with electronic (e.g., main controller 38) and electrical components (e.g., battery 37) of the handle assembly 20. The adapter assembly 30 includes a counterpart electrical connector 32 that is configured to engage the electrical receptacle 29. The electrical connector 32 also includes a plurality of electrical contacts 34 that engage and electrically connect to their counterpart electrical contacts 31.

With reference to FIG. 4, the trocar member 50 is slidably disposed within the tubular housing 30a of the adapter assembly 30 and extends past the distal end portion 30c thereof. In this manner, the trocar member 50 is configured for axial translation, which in turn, causes a corresponding axial translation of an anvil assembly 58 (FIG. 1) of the reload 40 to fire the staples (not shown) disposed therein. The trocar member 50 includes a proximal end which is coupled to the tubular housing 30a of the adapter assembly 30. A distal end portion of the trocar member 50 is configured to selectively engage the anvil assembly 58 of the reload 40 (FIG. 4). In this manner, when the anvil assembly 58 is connected to the trocar member 50, as will be described in detail hereinbelow, axial translation of the trocar member 50 in the first direction results in an opening of the anvil assembly 58 relative to the reload 40, and axial translation of the trocar member 50 in a second, opposite direction, results in a closing of the anvil assembly 58 relative to the reload 40.

The reload 40 is configured for operable connection to adapter assembly 30 and is configured to fire and form an annular array of surgical staples, and to sever a ring of tissue.

For a detailed description of an exemplary powered surgical stapler including an adapter assembly and a reload, reference may be made to commonly owned U.S. Patent Application Publication No. 2016/0310134 to Contini et al., titled "Handheld Electromechanical Surgical System," filed Apr. 12, 2016, incorporated in its entirety by reference herein.

With reference now to FIGS. 5-15, adapter assembly 30 includes an electrical assembly 100 disposed therewithin, and configured for electrical connection with and between handle assembly 20 and reload 40. Electrical assembly 100 provides for communication (e.g., identifying data, life-cycle data, system data, load sense signals) with the main controller 38 of the handle assembly 20 through the electrical receptacle 29 (FIG. 2).

Electrical assembly 100 includes the electrical connector 102; a proximal harness assembly 104, having a ribbon cable 105, connected to electrical connector 102; a distal harness assembly 106, having a ribbon cable 107, connected to proximal harness assembly 104; a load sensing assembly 108 connected to distal harness assembly 106; and a distal electrical plug assembly 110 also connected to distal harness assembly 106. The distal electrical plug assembly 110 is configured to selectively mechanically and electrically connect to a chip assembly (not shown) of reload 40.

Electrical connector 102 of electrical assembly 100 is supported within the proximal end portion 30b of the adapter assembly 30. Electrical connector 102 includes electrical contacts 102a which enable electrical connection to the handle assembly 20. Proximal harness assembly 104 is electrically connected to electrical connector 102 which is disposed on a printed circuit board 103.

The ribbon cable 105, 107 of respective proximal harness assembly 104 and distal harness assembly 106 of electrical assembly 100 includes a body or substrate suitable for supporting and/or electrically connecting electronic components thereto. The substrate of the ribbon cables 105, 107 is formed from one or more layers or sheets of dielectric material, such as a polymer or a ceramic, and one or more layers of conductive material, such as copper foil, that form conductive traces (not explicitly shown) in the substrate. Vias (not shown) may interconnect the conductive traces through different layers of the ribbon cables 105, 107.

In embodiments, the substrate of the ribbon cables 105, 107 is formed from copper-clade polyimides, such as PYRALUX® or NIKAFLEX®, which are registered trademarks owned by DuPont. In some embodiments, the substrate of the ribbon cables 105, 107 is formed from high temperature materials, such as PYRALUX® HT, also a registered trademark owned by DuPont.

In embodiment, it is contemplated that ribbon cables 105, 107 may be fabricated in whole, or in part, from liquid crystal polymer (LCP). LCP is more resistant to high PH environments and autoclave, as compared to ribbon cables without LCP. The ribbon cables 105, 107 may include multiple layers, for example, including a layer of polymide as an inner or outer layer. The multiple layers forming ribbon cables 105, 107 may be bonded using heat bonded lamination (e.g., melting/fusing the layers together) or by using an adhesive layer to bond the layers to one another. In other embodiments, the substrate of the ribbon cables 105, 107 is formed from copper-clade bonded to liquid crystal polymers (LCP) films.

It should be understood that the substrate of the ribbon cables 105, 107 is configured to allow for the fabrication of single or double sided flex circuits, multilayer flex circuits, and rigid flex circuits. The layers of the substrate of the ribbon cables 105, 107 may be joined to one another by, for example, laminating, welding, and/or using adhesives, among other methods and materials within the purview of those skilled in the art.

Plug assembly 110 includes a housing 112 defining a proximal facing bore 112a configured to receive a distal end portion 107a of the ribbon cable 107 of distal harness assembly 106. Electrical contacts or blades 114, 116 are supported within housing 112, with each electrical contact 114, 116 including a respective distal end portion 114a, 116a projecting distally from housing 112. Electrical contacts 114, 116 may be secured within bore 112a of housing 112 in any suitable manner, e.g., press-fit, friction-fit, snap-fit, tacked, welded, potted with a resin material or the like (for fluid-tight retention of electrical contacts 114, 116 within housing 112), glued, etc.

With reference to FIGS. 12A, 12B, 13 and 14, each electrical contact 114, 116 includes a pair of nubs 114c, 116c, respectively, formed in and/or projecting from respective proximal end portions 114b, 116b thereof. The nubs 114c, 116c defines solder areas for electrical connection to a distal end portion 107a of ribbon cable 107. Specifically, distal end portion 107a of ribbon cable 107 includes a first pair of soldering recess $107b_1$ formed in a first side edge thereof, and a second pair of soldering recess $107b_2$ formed in a second side edge thereof. The first pair of soldering recess $107b_1$ are configured to register with the pair of nubs 114c of electrical contact 114, and the second pair of soldering recess $107b_2$ are configured to register with the pair of nubs 116c of electrical contact 116. Each soldering recess of the first pair and the second pair of soldering recess $107b_1$, $107b_2$ may define solder pads (e.g., castellated type solder pads) for electrical connection with respective nubs 114c, 116c of electrical contacts 114, 116. It is contemplated that the distal end portion 107a of ribbon cable 107 may be soldered or secured to each electrical contact 114, 116 via an immersion tin process, electroless nickel immersion gold (ENIG) process, or the like know by those of skill in the art.

With reference to FIGS. 7-11, plug assembly 110 includes a seal member 120 disposed within a distal facing bore 112b (see FIG. 12A) of housing 112. Seal member 120 includes a pair of slots formed therein for passage of distal end portion 114a, 116a of electrical contacts 114, 116 therethrough. Seal member 120 is secured to a distal end of the housing 112 and includes a distal portion 120a that extends from the distal end of housing 112, and a proximal portion 120b that is configured to be received through at least one side surface of housing 112 and form an interlock therewith. Seal member 120 may include circumferential ridges 122 configured to engage an inner wall of a plug receptacle of reload 40 (not shown) to facilitate a friction fit and fluid-tight seal between plug assembly 110 of adapter assembly 30 and the plug receptacle of reload 40.

Seal member 120 may be formed of silicone, rubber, plastic, polymer, or any other suitable material.

As mentioned above, distal end portion 114a, 116a of electrical contacts 114, 116, respectively, of plug assembly 110, extend through and from seal member 120. The distal end portion 114a, 116a of electrical contacts 114, 116 are configured to electrically couple with respective contact members of a complimentary plug receptacle of reload 40 (not shown).

Figure 15:
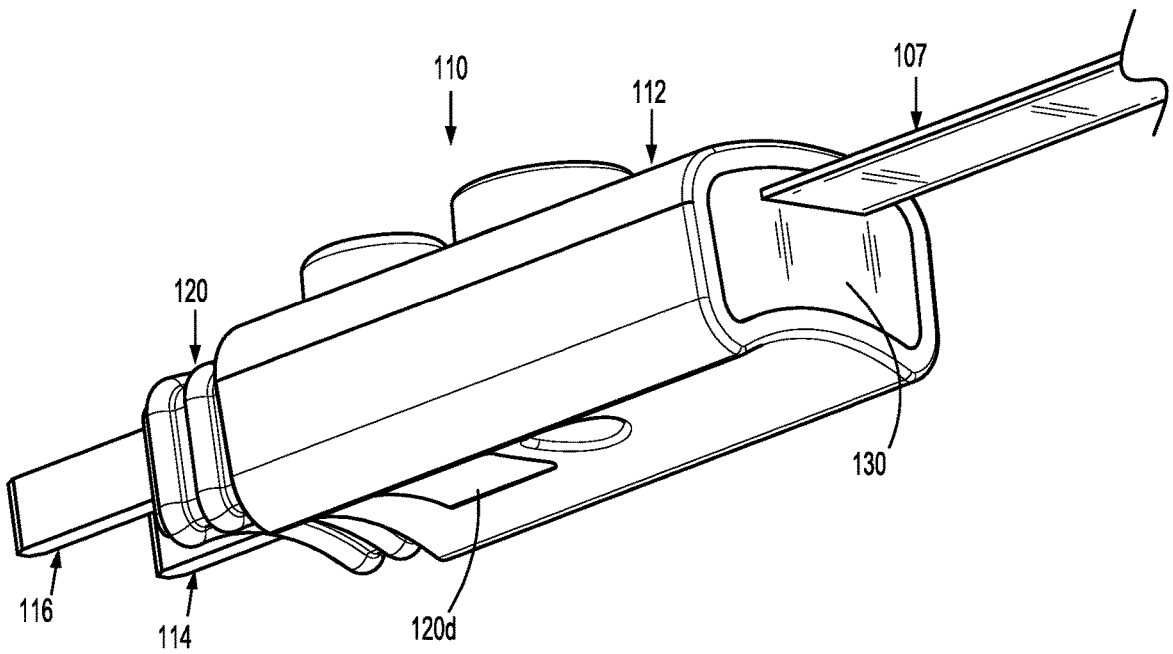
FIG. 15 is a rear, perspective view of the plug assembly of FIG. 8.

With reference to FIG. 15, with electrical contact 114, 116 and distal end portion 107a of ribbon cable 107 disposed within housing 112, proximal facing bore 112a of housing 112 may be filled with an encapsulating material 130 (e.g., resin, acrylic resin) which is resistant to disinfecting and sterilization operations (e.g., washing, rinsing, autoclaving, etc.).

Housing 112 may be transparent or near transparent, thereby enabling use of encapsulating materials 130 which are light or UV curable. The transparency of the housing 112 allows for the encapsulating material 130 to be cured after full assembly of plug assembly 110. Accordingly, housing 112 may be fabricated from polyphenylsulfone (PPSU) using an injection molding process, extrusion process, or the like, or polysulfone (PSU) which is also transparent for light/UV curing. In an embodiment, housing 112 may be fabricated from opaque materials providing that Room-Temperature-Vulcanizing (RTV) Encapsulates are selected that can cure without the need for UV or light cure processes.

Turning now to FIGS. 16-20, a plug assembly, in accordance with an alternate embodiment of the present disclosure, is generally designated as 210. Plug assembly 210 is substantially similar to plug assembly 110, and in the interest of brevity, only the differences therebetween will be described in detail herein below.

Figure 16:
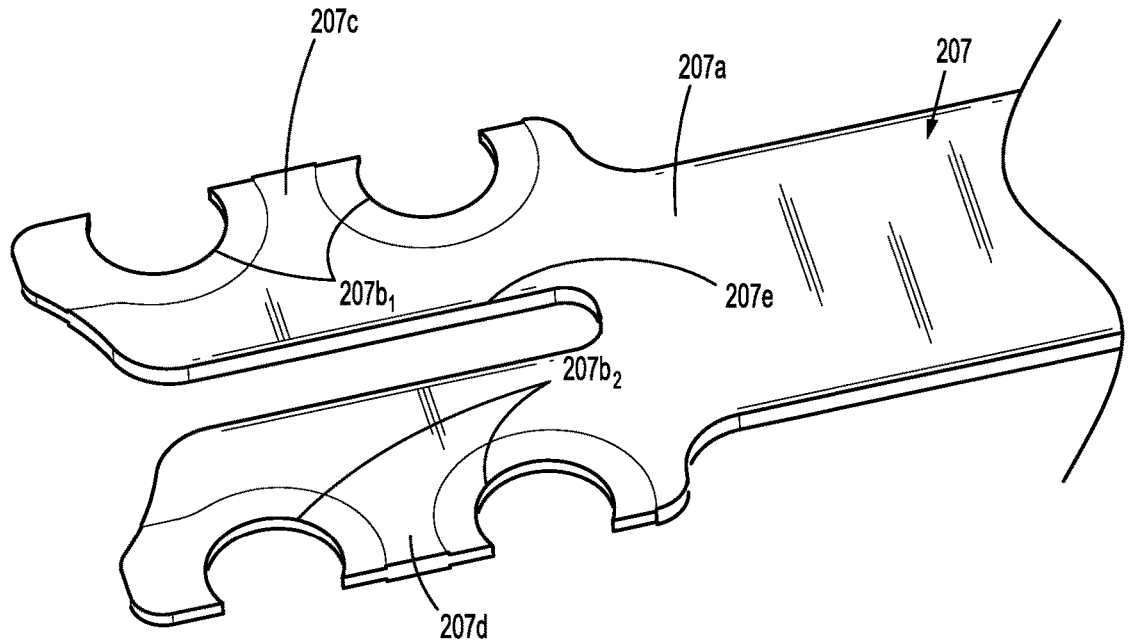
FIG. 16 is a perspective view of a distal end portion of a ribbon cable of another embodiment of a plug assembly, in accordance with the present disclosure.
Figure 17:
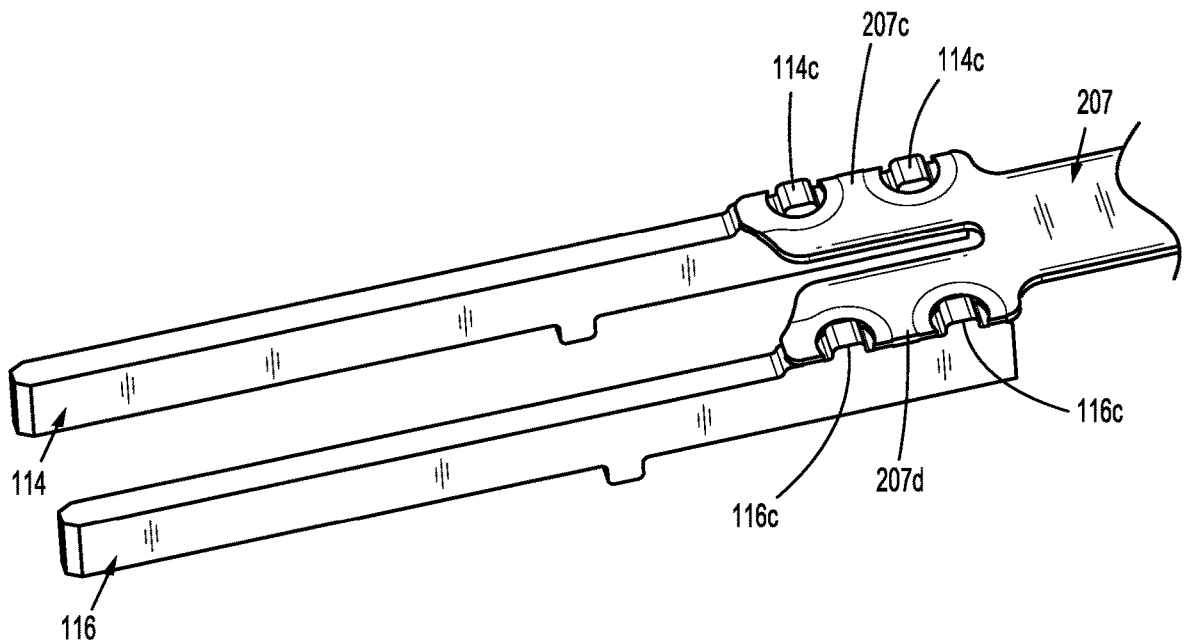
FIG. 17 is a perspective view of the distal end portion of the ribbon cable of FIG. 16, shown connected to a pair of electrical contacts of the plug assembly.
Figure 18:
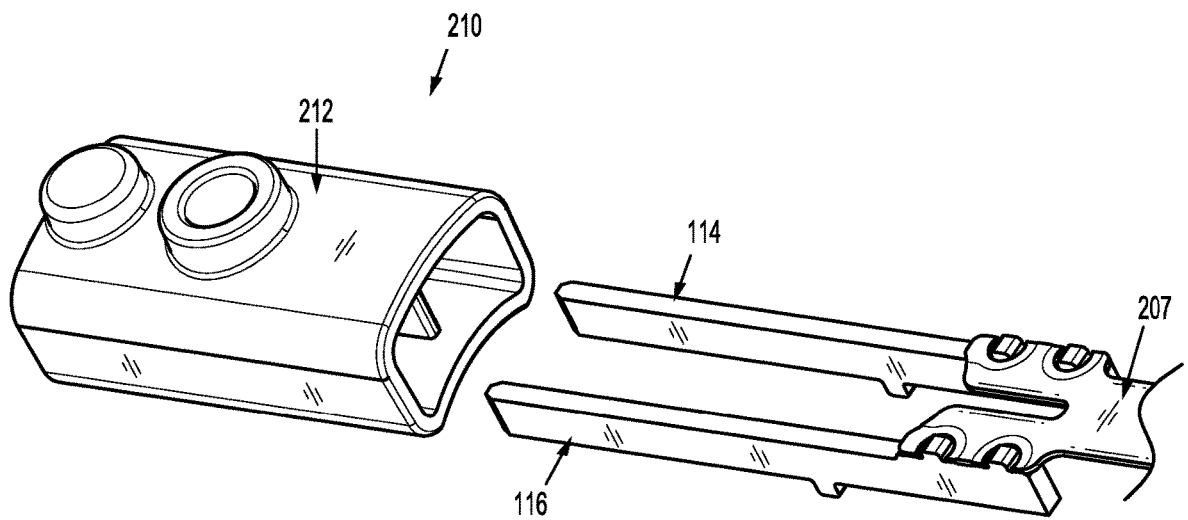
FIG. 18 is a rear, perspective view, with parts separated, of the pair of contacts and ribbon cable of FIGS. 16 and 17, and a housing of the plug assembly of FIGS. 16 and 17.

With reference to FIGS. 16-18, a distal end portion 207a of a ribbon cable 207 of an electrical assembly 100, for use with plug assembly 210, is shown and described. Distal end portion 207a of ribbon cable 207 is split, divided or bifurcated to include a pair of distally extending fingers 207c, 207d separated by a gap or space 207e.

Distal end portion 207a of ribbon cable 207 includes a first pair of soldering recess $207b_1$ formed in a first side edge of first finger 207c, and a second pair of soldering recess $207b_2$ formed in a second side edge of second finger 207d. The first pair of soldering recess $207b_1$ are configured to register with the pair of nubs 114c of electrical contact 114, and the second pair of soldering recess $207b_2$ are configured to register with the pair of nubs 116c of electrical contact 116. Each soldering recess of the first pair and the second pair of soldering recess $207b_1$, $207b_2$ may define solder pads (e.g., castellated type solder pads) for electrical connection with respective nubs 114c, 116c of electrical contacts 114, 116. It is contemplated that first and second fingers 207c, 207d of distal end portion 207a of ribbon cable 207 may be soldered or secured to each electrical contact 114, 116, respectively, via an immersion tin process, electroless nickel immersion gold (ENIG) process, or the like know by those of skill in the art.

Figure 19:
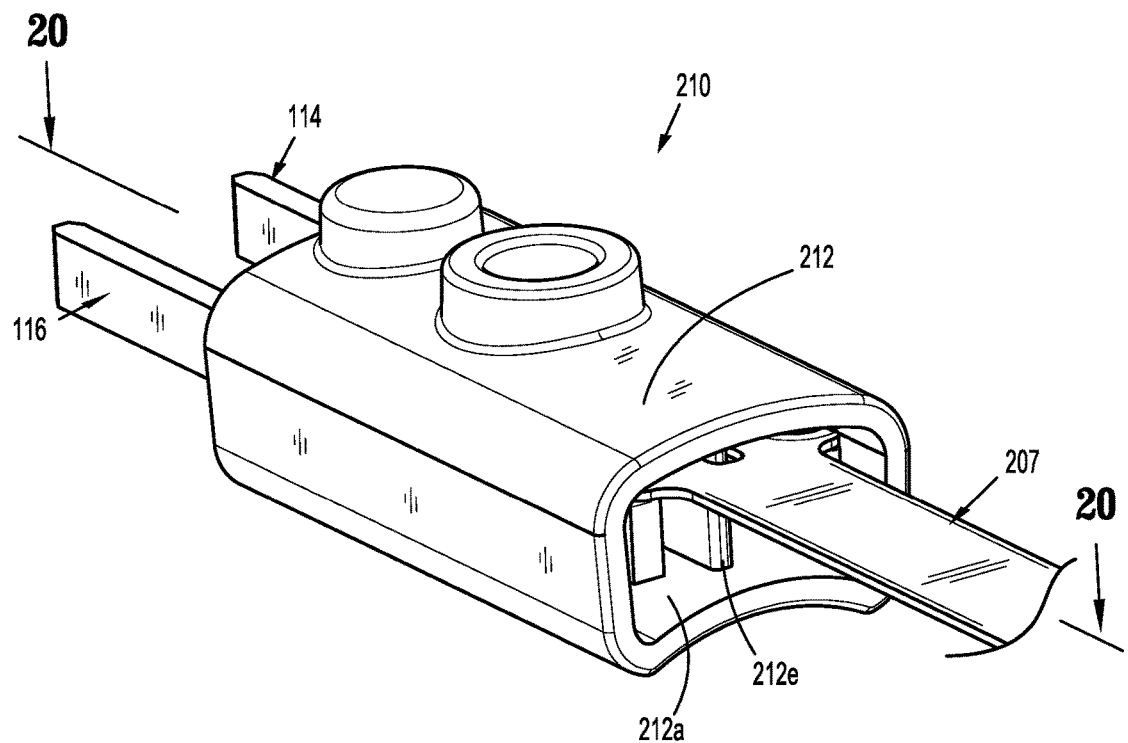
FIG. 19 is a rear, perspective view, with parts assembled, of the pair of contacts and ribbon cable of FIGS. 16 and 17, and a housing of the plug assembly of FIGS. 16 and 17.
Figure 20:
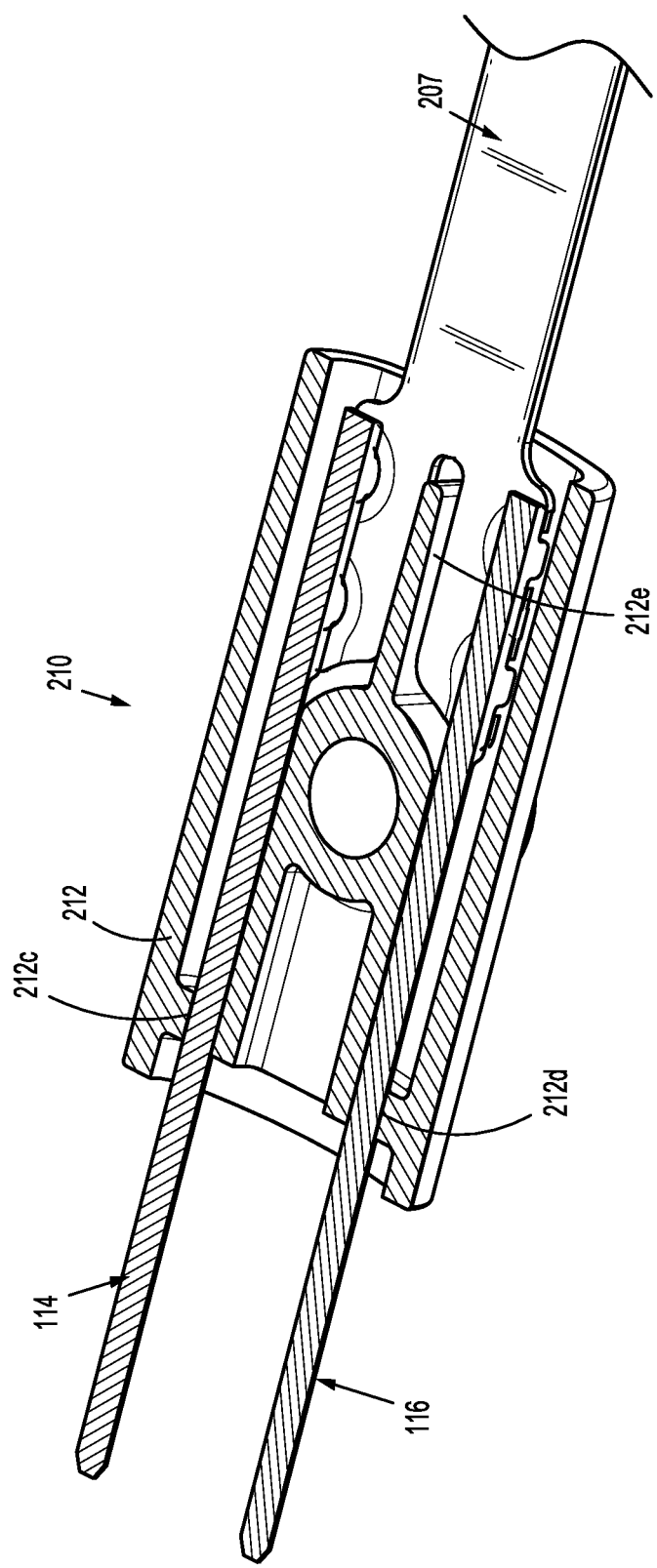
FIG. 20 is a cross-sectional view of the plug assembly, as taken through 20-20 of FIG. 19.

With reference now to FIGS. 18-20, a housing 212 of plug assembly 210, is shown and described. Housing 212 defines a proximal facing bore 212a configured to receive a distal end portion 207a of ribbon cable 207. Electrical contacts or blades 114, 116 are supported within housing 112, with each electrical contact 114, 116 including a respective distal end portion 114a, 116a disposed within respective lumens 212c, 212d (FIG. 20) defined therewithin, and projecting distally from housing 212. Electrical contacts 114, 116 may be secured within bore 212a of housing 212 in any suitable manner, e.g., press-fit, friction-fit, snap-fit, tacked, welded, potted with a resin material or the like (for fluid-tight retention of electrical contacts 114, 116 within housing 212), glued, etc.

Housing 212 includes a central, proximally extending rib or wall 212e disposed within proximal facing bore 212a. Rib 212e is configured and dimensioned to substantially fill gap 207e defines in distal end portion 207a of ribbon cable 207 (as described above), when electrical contacts 114, 116 and distal end portion 207a of ribbon cable 207 are seated within housing 212. Rib 212e may be an integral component of housing 212, and thus, may be constructed from the same conducting resistant material as housing 212. It is contemplated, in accordance with the present disclosure, that rib 212e may work in combination with the encapsulating material 130 (e.g., resin, acrylic resin) of proximal facing bore 212a to resist ingress of moisture into plug assembly 210, and resist shorting of the solder pads defined by the first pair and the second pair of soldering recess $207b_1$, $207b_2$ of distal end portion 207a of ribbon cable 207.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A plug assembly for an electromechanical surgical system, the plug assembly comprising:
   a housing defining a proximal facing bore and a distal facing bore, the housing including a proximally and longitudinally extending central rib located within the proximal facing bore;
   a pair of electrical contacts disposed within the housing, wherein the pair of electrical contacts are spaced apart from one another, each electrical contact including:
      a distal end portion projecting distally from a distal end of the housing; and
      a proximal end portion disposed within the proximal facing bore of the housing;
   a ribbon cable having an axially split distal end portion defining a pair of fingers spaced apart from one another by a gap, each finger being electrically connected to the proximal end portion of a respective one of the pair of electrical contacts, and being disposed with the proximal facing bore of the housing, wherein the rib of the housing is disposed within the gap of the ribbon cable;
   an encapsulating material filling the proximal facing bore of the housing; and
   a seal member disposed within the distal facing bore of the housing, wherein the housing and the seal member form a fluid-tight seal therebetween, wherein the seal member includes a distal portion projecting distally from the housing, and a proximal portion extending from a side surface of the housing.

2. The plug assembly according to claim 1, wherein the housing is at least partially transparent.

3. The plug assembly according to claim 2, wherein the housing is fabricated from polyphenylsulfone (PPSU) or polysulfone (PSU).

4. The plug assembly according to claim 1, wherein the housing is transparent for light or UV curing.

5. The plug assembly according to claim 4, wherein the encapsulating material is a light or UV curable material.

6. The plug assembly according to claim 5, wherein the encapsulating material is resin or acrylic resin.

7. The plug assembly according to claim 1, wherein the seal member is fabricated from silicone, rubber, plastic or polymer.

8. The plug assembly according to claim 1, wherein the distal end portion of each of the pair of electrical contacts extends distally beyond the seal member.

9. The plug assembly according to claim 8, wherein the seal member includes at least one circumferential ridge extending therearound.

10. A plug assembly for an electromechanical surgical system, the plug assembly comprising:
    a housing defining a proximal facing bore, the housing including a proximally and longitudinally extending central rib located within the proximal facing bore;
    a pair of electrical contacts disposed within the housing, wherein the pair of electrical contacts are spaced apart from one another, each electrical contact including:
       a distal end portion projecting distally from a distal end of the housing; and
       a proximal end portion disposed within the proximal facing bore of the housing, wherein each electrical contact includes a nub projecting from the proximal end portion thereof;
    a ribbon cable having an axially split distal end portion defining a pair of fingers spaced apart from one another by a gap, each finger being electrically connected to the proximal end portion of a respective one of the pair of electrical contacts, and being disposed with the proximal facing bore of the housing, wherein the rib of the housing is disposed within the gap of the ribbon cable, wherein each finger of the distal end portion of the ribbon cable defines a respective solder recess formed therein for receipt of a respective nub; and
    an encapsulating material filling the proximal facing bore of the housing.

11. A plug assembly for an electromechanical surgical system, the plug assembly comprising:
    a housing defining a proximal facing bore, the housing including a proximally and longitudinally extending central rib located within the proximal facing bore;
    a pair of electrical contacts disposed within the housing, wherein the pair of electrical contacts are spaced apart from one another, each electrical contact including:
       a distal end portion projecting distally from a distal end of the housing; and
       a proximal end portion disposed within the proximal facing bore of the housing, wherein each electrical contact includes a pair of nubs projecting from the proximal end portion thereof;
    a ribbon cable having an axially split distal end portion defining a pair of fingers spaced apart from one another by a gap, each finger being electrically connected to the proximal end portion of a respective one of the pair of electrical contacts, and being disposed with the proximal facing bore of the housing, wherein the rib of the housing is disposed within the gap of the ribbon cable, wherein each finger of the distal end portion of the ribbon cable defines a respective pair of solder recesses formed therein for receipt of a respective pair of nubs; and
    an encapsulating material filling the proximal facing bore of the housing.

12. The plug assembly according to claim 11, wherein the housing is transparent for light or UV curing.

13. The plug assembly according to claim 12, wherein the housing is fabricated from polyphenylsulfone (PPSU) or polysulfone (PSU).

14. The plug assembly according to claim 13, wherein the encapsulating material is a light or UV curable material.

15. The plug assembly according to claim 14, wherein the housing defines a distal facing bore therein; and wherein the plug assembly further comprises:
    a seal member disposed within the distal facing bore of the housing, wherein the housing and the seal member form a fluid-tight seal therebetween.

16. The plug assembly according to claim 15, wherein the seal member includes a distal portion projecting distally from the housing, and a proximal portion extending from a side surface of the housing.

17. The plug assembly according to claim 16, wherein the distal end portion of each of the pair of electrical contact extends distally beyond the seal member, and wherein the seal member includes at least one circumferential ridge extending therearound.

* * * * *